US012611537B2

(12) United States Patent
Schweinzger et al.

(10) Patent No.: US 12,611,537 B2
(45) Date of Patent: Apr. 28, 2026

(54) CERAMIC ELECTRODE, ASSEMBLY COMPRISING THE CERAMIC ELECTRODE, ARRANGEMENT COMPRISING THE CERAMIC ELECTRODE, AND METHOD OF MANUFACTURING A CERAMIC ELECTRODE

(71) Applicant: TDK Electronics AG, Munich (DE)

(72) Inventors: Manfred Schweinzger, Bad Schwanberg (AT); Stefan Obermair, Stainz (AT)

(73) Assignee: TDK Electronics AG, Munich (DE)

( * ) Notice: Subject to any disclaimer, the term of this patent is extended or adjusted under 35 U.S.C. 154(b) by 371 days.

(21) Appl. No.: 18/256,060

(22) PCT Filed: Nov. 29, 2021

(86) PCT No.: PCT/EP2021/083333
§ 371 (c)(1),
(2) Date: Jun. 6, 2023

(87) PCT Pub. No.: WO2022/122445
PCT Pub. Date: Jun. 16, 2022

(65) Prior Publication Data
US 2024/0058597 A1      Feb. 22, 2024

(30) Foreign Application Priority Data
Dec. 11, 2020      (DE) .......................... 102020133165.7

(51) Int. Cl.
*A61N 1/04*      (2006.01)
*B32B 18/00*      (2006.01)

(52) U.S. Cl.
CPC ............ *A61N 1/0472* (2013.01); *B32B 18/00* (2013.01); *B32B 2255/205* (2013.01); *B32B 2457/00* (2013.01)

(58) Field of Classification Search
None
See application file for complete search history.

(56) References Cited

U.S. PATENT DOCUMENTS 4,011,861 A * 3/1977 Enger .................... A61B 5/076
607/121
6,417,621 B1 7/2002 Hennings et al.
(Continued)

FOREIGN PATENT DOCUMENTS

AT          15889 U1      8/2018
DE 102011119125 A1      5/2013
(Continued)

OTHER PUBLICATIONS

International Search Report (Form PCT/ISA/210) for International Patent Application No. PCT/EP2021/083333, issued from the International Searching Authority, date of mailing Jul. 15, 2022, with English-language translation, 12 pages.
(Continued)

*Primary Examiner* — Michael W Kahelin
(74) *Attorney, Agent, or Firm* — ICE MILLER LLP; Justin D. Swindells

(57) ABSTRACT
A ceramic electrode comprising a support member as a mechanically stabilizing component, a dielectric layer having a thickness (D) which is less than or equal to 150 μm, and an electrode layer.

26 Claims, 6 Drawing Sheets

(56)  References Cited

U.S. PATENT DOCUMENTS

| | | | |
|---|---|---|---|
| 6,445,940 | B1 | 9/2002 | Gevins et al. |
| 7,016,725 | B2 | 3/2006 | Palti |
| 2003/0150372 | A1 | 8/2003 | Palti |
| 2004/0094417 | A1* | 5/2004 | Noda ................ G01N 27/4073 |
| | | | 204/426 |
| 2009/0076366 | A1 | 3/2009 | Palti |
| 2014/0328004 | A1 | 11/2014 | Specht et al. |
| 2015/0314131 | A1 | 11/2015 | Stevenson et al. |
| 2016/0346361 | A1 | 12/2016 | Quake et al. |
| 2016/0346536 | A1 | 12/2016 | Palti et al. |
| 2020/0171297 | A1 | 6/2020 | Kirson et al. |
| 2021/0078907 | A1 | 3/2021 | Schweinzger |
| 2021/0187831 | A1* | 6/2021 | Jung ...................... A61B 5/263 |

FOREIGN PATENT DOCUMENTS

| | | | |
|---|---|---|---|
| EP | 1043751 | A1 | 10/2000 |
| JP | 2001319966 | A | 11/2001 |
| JP | 2018110651 | A | 7/2018 |
| KR | 20010001306 | A | 5/2001 |
| WO | 2005115535 | A2 | 12/2005 |
| WO | 2008087489 | A2 | 7/2008 |
| WO | 2019174719 | A1 | 9/2019 |
| WO | 2020110050 | A1 | 6/2020 |

OTHER PUBLICATIONS

Written Opinion of the International Searching Authority (Form PCT/ISA/237) for International Patent Application No. PCT/EP2021/083333, issued from the International Searching Authority, date of mailing Jul. 15, 2022, with English-language translation, 22 pages.
International Preliminary Report on Patentability (Form PCT/IB/373) for International Patent Application No. PCT/EP2021/083333, issued from the International Bureau of WIPO, date of mailing Jun. 13, 2023, with English-language translation, 13 pages.

* cited by examiner

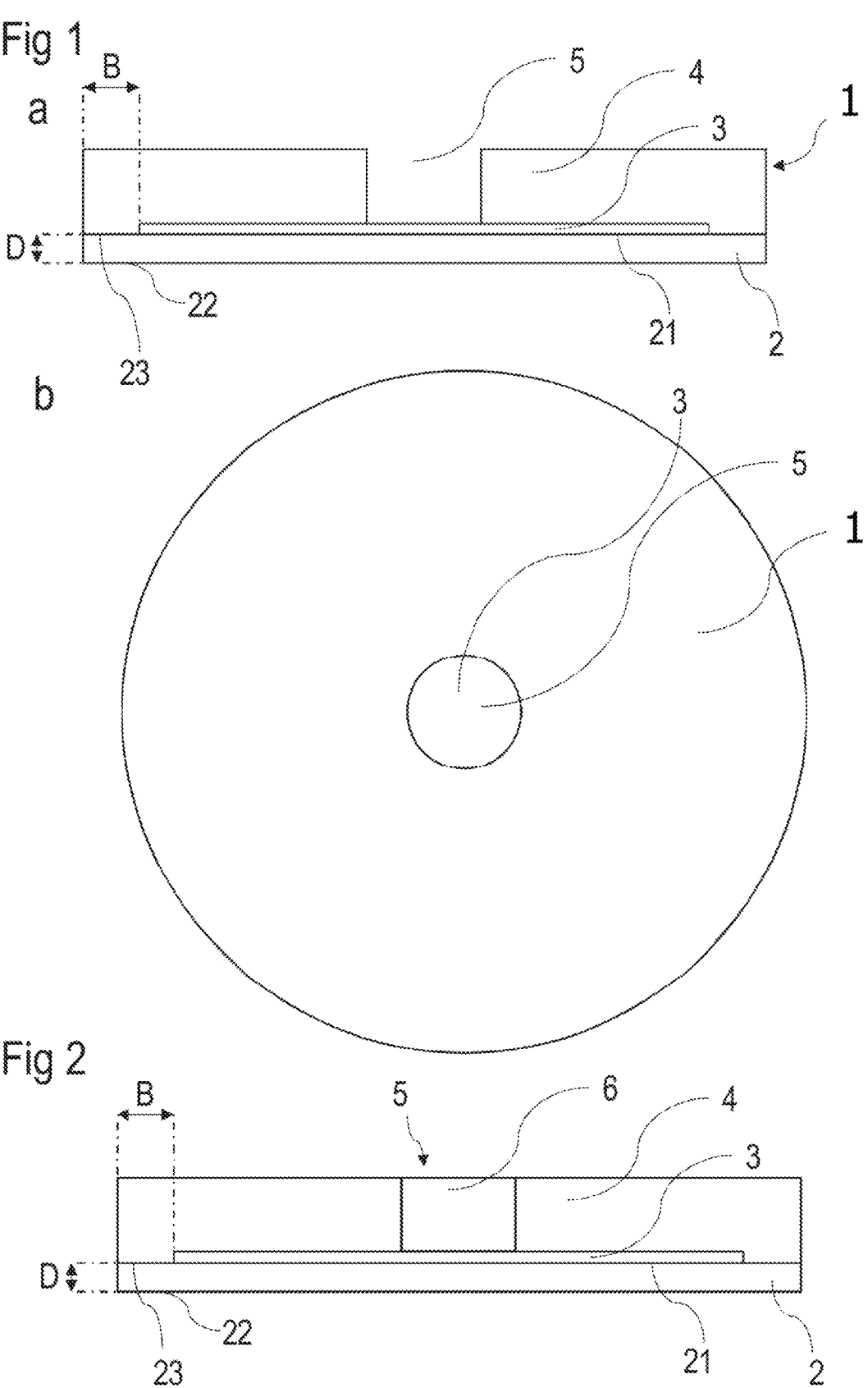

Fig 8
a
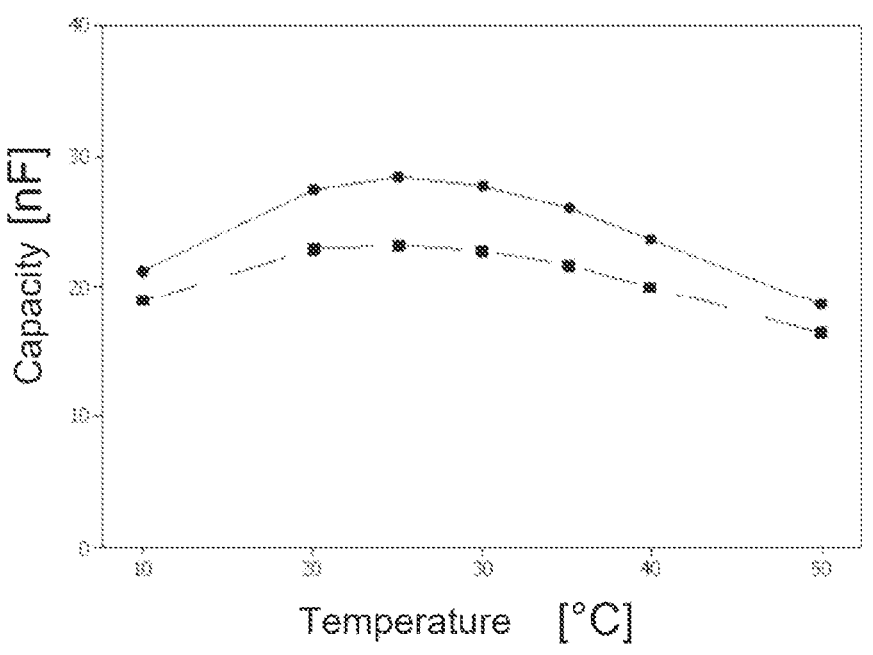
b
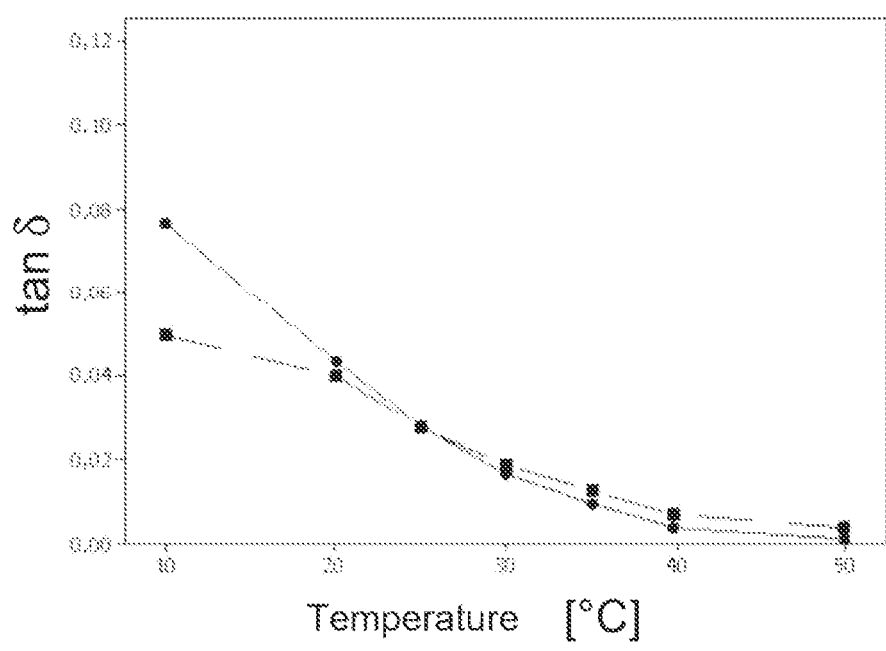

Fig 9
a
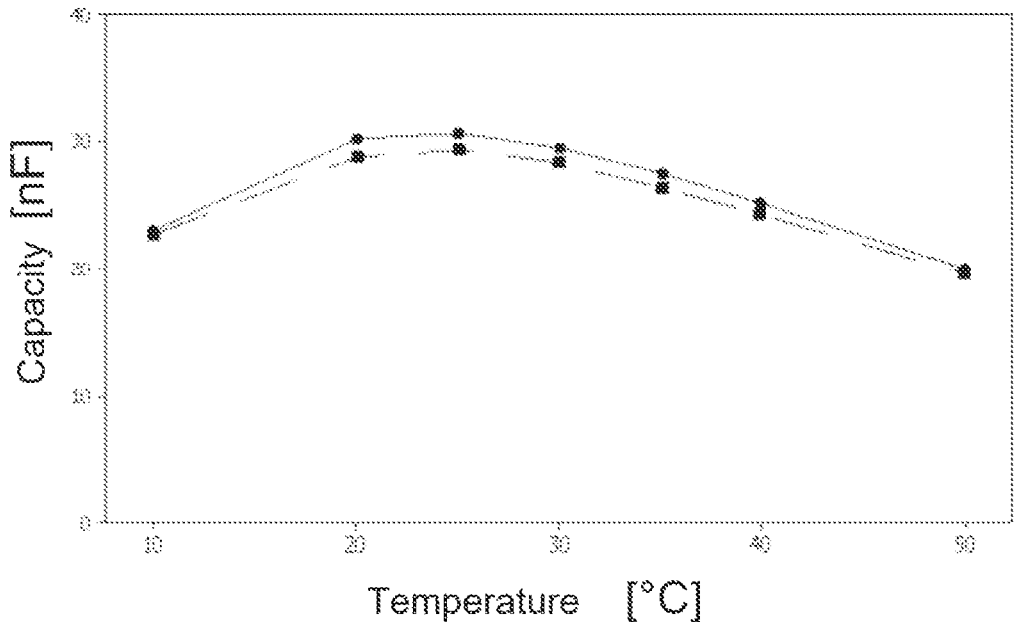
b
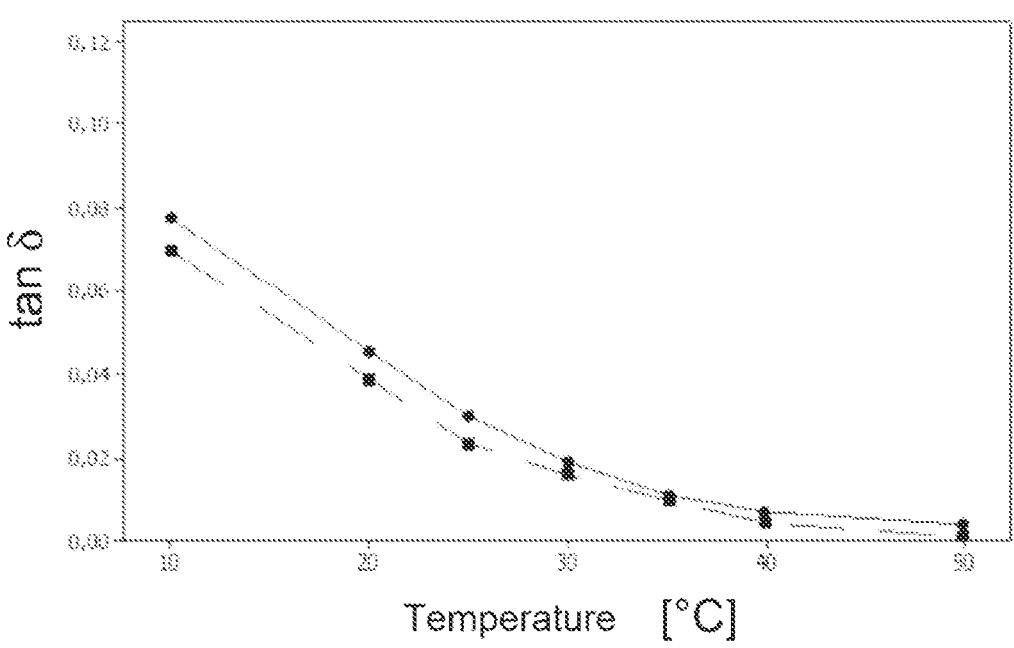

CERAMIC ELECTRODE, ASSEMBLY COMPRISING THE CERAMIC ELECTRODE, ARRANGEMENT COMPRISING THE CERAMIC ELECTRODE, AND METHOD OF MANUFACTURING A CERAMIC ELECTRODE

CROSS-REFERENCE TO RELATED APPLICATIONS

This application is a 371 national phase application of International Application No. PCT/EP2021/083333, filed on Nov. 29, 2021, which published in the German language on Jun. 16, 2022, under International Publication No. WO 2022/122445 A2, which claims priority to Germany Patent Application No. 102020133165.7, filed on Dec. 11, 2020. Each disclosure is incorporated herein by reference in its entirety.

DESCRIPTION

Ceramic electrode, assembly comprising the ceramic electrode, arrangement comprising the ceramic electrode, and method of manufacturing a ceramic electrode The invention relates to a ceramic electrode suitable for applying high-frequency alternating fields to the human body or the body of a mammal. Furthermore, the invention relates to a method of manufacturing such an electrode. Finally, the invention relates to an assembly comprising the ceramic electrode and an assembly comprising a plurality of ceramic electrodes.

Cell division in organisms can be inhibited by exposing the cells to high-frequency alternating electric fields. This principle can be used to treat a number of tumor types by inhibiting the rapid and uncontrolled cell division of tumor cells using high-frequency alternating electric fields. In particular, the alternating fields affect proteins that are involved in cell division and prevent them from functioning. Corresponding procedures have been approved by the US Food & Drug Administration (FDA). The high-frequency alternating electric fields used to combat tumor cells are also known as "tumor-treating fields" (TTF). They are transmitted to the patient by means of electrodes placed around the body region affected by the tumor. In particular, the application to date has been directed primarily at the treatment of brain tumors, but can in principle also be applied to other types of cancer or tumor.

Selectivity for different cell types can be achieved by choosing suitable frequencies. This reduces the side effects of the therapy. Examples of methods and devices for destroying uncontrollably dividing cells can be found, for example, in US patent application US 2003/0150372 A1 and patent U.S. Pat. No. 7,016,725 B2.

In the methods described, the electrodes are of special importance by which the high-frequency alternating electric fields are transmitted to the organism to be treated. Ceramic electrodes are particularly preferred for this purpose. These include a dielectric layer made of a ceramic material with a high dielectric constant.

For example, from the Austrian utility model GM 50248/2016 or from the PCT patent application WO 2019174719 for such an application, a polycrystalline ceramic solid having a main phase of the following general formula is known: $(1-y)Pb_a(Mg\ Nb_{bc})O_{3-e}+yPb_aTidO_3$ Current ceramic electrodes prior to the present invention typically have electrode areas on a scale of 250 mm² or even larger.

In this context, however, the inventors have recognized that ceramic electrodes of such a size are poorly matched to the surfaces to be applied, such as a patient's head. This problem is particularly apparent at body sites with highly curved surfaces, such as the head, or at other sites with profiles that challenge out. Ceramic electrodes that are too large can result in poor wearing comfort. In addition, it is usually necessary to work with larger quantities of a contact gel.

To this end, the inventors further recognized that smaller electrodes can achieve better matching to rounded or otherwise challengingly profiled application sites.

This task is solved by an electrode according to claim 1. Further advantageous embodiments can be taken from the further claims.

As a first aspect of the invention, a ceramic electrode is proposed which includes a support element as a mechanically stabilizing component, a dielectric layer having a thickness (D) less than or equal to 150 µm, and an electrode layer.

With such a thin dielectric layer, it is possible to miniaturize or reduce the size of electrodes, for example for the above-mentioned applications, while at the same time maintaining high capacitance values of 20 to 50 nF, for example. Here, the electrode area can be reduced by a factor of 10 to 50 compared with conventional electrodes, for example, by lowering the dielectric thickness from the previous standard of about 1 mm to a value less than or equal to 150 µm, i.e., by about an order of magnitude less. Thus, a significant reduction in the size and weight of the individual electrode can be achieved while maintaining the high capacitance values.

However, the inventors of the present invention have recognized here that the formation of such a thin dielectric layer may involve the difficulty that the necessary stability for an application is no longer given. To solve this problem, the invention proposes a functional separation between a structure-providing component, in this case the support element, and the dielectric component, i.e., the dielectric layer.

Here, the support element is configured to provide a sufficient degree of mechanical stability to the ceramic electrode. As shown below, the support element may, for example, be firmly baked to the electrode layer and/or the dielectric layer to achieve this function. The support element may also, for example, contain or be made of a ceramic material similar to that of the dielectric layer.

Preferably, the support element has a thickness, that is, an extension in the direction corresponding to the thickness direction of the dielectric layer, which is at least equal to the thickness of the dielectric layer. More preferably, the thickness of the support element is significantly greater.

In principle, the support element can have any shape as long as the function of mechanically stabilizing the thin dielectric layer is fulfilled.

The support element is preferably arranged on the side of the dielectric layer on which the electrode layer is also arranged. This has the advantage for the application that the dielectric layer can be in direct contact with the surface in an application where, for example, a tumor is to be treated. For example, the dielectric layer should face a patient.

In principle, the support element can be designed so that its surface overlaps with a large part of the dielectric layer. In such a configuration, this can provide the advantage that only a small portion of the dielectric layer is freestanding. A too large freestanding area may be more fragile.

Alternatively, the support element may be formed on only portions of the surface, which additionally allows for weight reduction that may also increase a patient's comfort during an application.

According to a preferred aspect of the ceramic electrode, the electrode layer is disposed on a first surface of the dielectric layer, wherein the electrode layer partially covers the dielectric layer. This means that, in this aspect, a free area of the first surface of the dielectric layer is free of the electrode layer. The support element is in contact with this free area.

The dielectric layer in the sense of the present invention is preferably planar. That is, the extent in the lateral direction, i.e. a direction perpendicular to the thickness direction, is significantly greater than the extent in the thickness direction. Likewise, the electrode layer is preferably formed planar.

The free area can be a contiguous region of the first surface of the dielectric layer. However, it can also be composed of areas spatially separated from one another, for example by the support element.

By leaving a free area free of the electrode layer on the first surface of the dielectric layer on which the electrode layer is arranged, it is possible for the support element to be in contact with it. Since the support element can preferably also consist of a ceramic material, or can also consist of the same material as the dielectric layer, a particularly good mechanical contact or bond between the support element and the dielectric layer can be achieved in this way.

The electrode can preferably be manufactured by sintering, so that in a sintering process, for example as described below, a particularly efficient bonding of the dielectric layer in the free areas with the support element can be achieved. This enables the support element to perform its function as a stabilizing component particularly well.

Here, the support element can cover part of the free area or the entire free area.

The support element can also be additionally formed in the area of the electrode layer.

According to another preferred aspect, the free area of the first surface of the dielectric layer is a lateral edge region of the first surface of the dielectric layer.

The dielectric layer has an edge, i.e. an end of the extension of the dielectric layer in the lateral direction. Here, the lateral edge region can be understood to refer to a partial region or a region of the first surface that is in contact with this edge.

For example, the lateral edge region may also be formed to extend along the entire edge of the dielectric layer. That is, the lateral edge region may frame an inner region of the first surface of the dielectric layer. Preferably, the electrode layer is formed on this inner region. That is, the lateral edge region can, for example, frame the region which is covered by the electrode layer.

In that the support element is at least partially formed in this free area, which in this preferred embodiment is a lateral edge region, the support element can form a frame-like structure, which can thus ensure the mechanical stability of the ceramic electrode in a particularly favorable manner.

According to a further preferred aspect of the ceramic electrode, the free area, which may preferably also be a lateral edge region, has a width greater than or equal to the thickness D in the dielectric layer. Here, a width may be understood as an extension in the lateral direction.

The inventors of the present invention have found that when the free area has a width that is at least the thickness of the dielectric layer with respect to its amount, and the support member is formed at least partially on this free area, the mechanical stability or structure of the ceramic electrode can be efficiently supported and reinforced.

According to a further preferred aspect, the width of the support element is greater than or equal to the thickness of the dielectric layer. Here, too, a width can be understood as an extension in the lateral direction.

With this minimum width, the support element can efficiently support the ceramic electrode in its stability.

In particular, the support element can preferably have at least the dimensions of the free area in at least one spatial direction.

This means, for example, in the case that the support element forms a frame or a partial frame, the thickness can be a local direction measured from the edge of the electrode layer to the closest possible point of the edge of the dielectric layer. In this case, this definition can apply both to the lateral edge region of the first surface of the dielectric layer and to a support element formed thereon or in parts of such a region.

According to a further preferred aspect, the ceramic electrode comprises a contact component. This contacts the electrode layer.

Preferably, a ceramic electrode can be electrically contacted from outside on this contact component. This is therefore suitable for transmitting an alternating field to the electrode layer, for example.

For example, the contact component may be in the form of a via. This may be, for example, in a case where the support element covers a major portion of the dielectric layer with the electrode layer thereon. Such a via may preferably be arranged to be in direct contact with the electrode.

In such a case, the side of the via that is not in contact with the electrode layer can have a surface that, for example, terminates with one side of the support element. This can, for example, enable soldering on further components such as a flexible board.

Alternatively, the contact component can be a contact layer. This can be formed on a surface of the support element that is angled away from the dielectric layer and thus serve as a contact surface in applications. In such a case, the contact component can make contact with an electrode via a cavity.

According to another aspect of the ceramic electrode, the thickness D is between 20 μm and 100 μm. Even more preferably, the thickness D is between 30 μm and 80 μm. For example, the thickness D may be 40 to 60 μm.

In the above thickness range, it can be achieved that the electrode is not too thin and thus too fragile. The inventors of the present invention have found that in many cases an electrode thickness below 20 μm hardly has the necessary stability even in the presence of a support element, since the grain size of preferred ceramic materials for the dielectric layer is on a scale of a few micrometers to a few tens of micrometers. This means that below 20 μm the layers can only consist of individual crystal grains in the thickness direction, which impairs their stability too much even with a support element.

In addition, if the electrode is too thin, the insulating property of the dielectric layer cannot be guaranteed to a sufficiently high degree.

The dielectric layer should be able to withstand operating voltages of at least 150 V. For safety reasons, it must preferably also be possible to maintain an insulation strength of up to 500 V, since possible overvoltages in this range must not be allowed to flash over to a patient.

The above advantages can be achieved even better if the thicknesses are at least 30 μm or even 40 μm.

Furthermore, the inventors of the present invention have found that at a thickness of 100 μm or below, an even more significant reduction in electrode area is possible. Thus, this effect can be achieved to an even better extent at an electrode thickness of 80 μm or below, or at an electrode thickness of 60 μm or below, respectively.

According to a preferred aspect of the ceramic electrode, the dielectric layer comprises a ceramic material having a dielectric constant of ≥15000.

Such high dielectric constants of over 15000, preferably in a temperature range between 30 and 42° C., make it possible to produce high-capacity electrodes which are also suitable for miniaturization.

Preferably, the ceramic material has a dielectric constant of 25000 or higher, or more preferably 40000 or higher.

Furthermore, the ceramic material preferably exhibits loss factors below 0.2, more preferably below 0.12, and even more preferably below 0.05 in the above temperature range.

Preferably for a ceramic electrode such a high dielectric constant can be achieved for a ceramic material selected from $(1-y)[Pb_a(Mg_bNb_c)O_{3-e}]+y[Pb_aTi_dO_3]$ and $Ba_m(Ti_n Zr_p)O_3$ with a doping comprising manganese and a rare earth element.

For $(1-y)[Pb_a(Mg_b Nb_c)O_{3-e}]+y[Pb_aTi_dO_3]$ is preferred:
$0.055 \leq y \leq 0.065$;
$0.95 \leq a \leq 1.02$;
$0.29 \leq b \leq 0.36$;
$0.63 \leq c \leq 0.69$;
$0.9 \leq d \leq 1.1$;
$0 \leq e \leq 0.1$.

The substance $Ba_m(Ti_n Zr_p)O_3$ preferentially fulfills the conditions:
$0.95 \leq m \leq 1.05$;
$0.8 \leq n \leq 0.9$;
$0.1 \leq p \leq 0.2$;
$m < n + p$.

As described above, this material is doped with manganese and rare earth elements. A proportion of manganese can be defined here as x and a proportion of rare earth elements can be defined here as z. Thus here preferably further applies:
$0.0005 \leq x \leq 0.01$;
$0.001 \leq z \leq 0.05$.

With a ceramic material of the formula $(1-y)[Pb_a(Mg_bNb_c)O_{3-e}]+y[Pb_aTi_dO_3]$ dielectric constants on a scale of 15000 to 25000 can be achieved.

With a ceramic material of the formula $Ba_m(Ti_n Zr_p)O_3$ even dielectric constants on a scale of 20000 to 40000 can be achieved.

Preferably, the ceramic electrode has the following dimensions. For example, the ceramic electrode may have a cross-sectional area in the range of 15 to 100 mm². A maximum thickness may be, for example, 300 to 700 μm.

The maximum thickness can be understood as the largest extension in a direction perpendicular to the plane of extension of the dielectric layer.

Even more preferably, a base area or a cross-sectional area of the ceramic electrode is in the range 20 to 70 mm², preferably in the range 20 to 50 mm², and even more preferably in the range 25 to 40 mm². For example, the cross-sectional area may be 25 mm 2 or 36 mm². For example, a maximum thickness can be between 400 and 600 μm, for example 500 μm.

The cross-sectional area or the base area of the ceramic electrode formed in this way preferably corresponds to the area of the dielectric layer. The shape of this is basically not limited. Preferably, however, it is either circular, rectangular or square.

The circular shape may be particularly preferred for applications because it avoids sharp edges or corners. Corners can have a tendency to break. In addition, round shapes can increase carrying comfort.

Rectangular or square features may be preferred in terms of a manufacturing process as described below, especially when structured patterns are applied.

The above dimensions are preferred to achieve good comfort in use, for example in cancer therapy, as this makes the electrode sufficiently small that it does not protrude from a structurally challenging full or round surface, such as a patient's head.

Preferably, then, the ceramic electrode is configured and suitable for attachment to the human body or parts of the human body.

According to a further preferred embodiment, the ceramic electrode may have one or more cavities, which are preferably formed in the support element.

In particular, a regular pattern of cavities may preferably be formed in the support element. For example, a grid can be formed by the support element, which frames individual cavities.

In such a way, the weight of the ceramic electrode can be kept low, while alternating structures of support element and cavities can ensure higher stability than for a case in which the same mass of support element is applied and it encloses a single larger cavity.

In accordance with another aspect of the invention, there is disclosed an assembly comprising a ceramic electrode disposed on a flexible circuit board in accordance with the embodiments shown above.

This means that the ceramic electrode according to the invention can be part of an assembly according to the invention, whereby a flexible board can also establish an external electrical contact, for example, via the contact component as described above.

The attachment of the ceramic electrode in the assembly on a flexible board can be formed, for example, via soldering.

The flexibility of the board may be preferred for use on patients, as it allows adaptation to the body surface. Flexible can be regarded as bendable or having a certain softness.

According to a further aspect of the invention, there is provided an arrangement which is an array, comprising either a plurality of ceramic electrodes as described above, or a plurality of previously described assemblies.

For example, nine or eighteen ceramic electrodes may be arranged in such an arrangement or array.

Such an array may be designed to flexibly conform to the surface of a patient's body, as the electrodes are greatly reduced in size compared to what was available prior to the invention, allowing flexibility in the areas between the electrodes.

In accordance with another aspect of the invention, a method of making a ceramic electrode that can be used to make a previously described ceramic electrode is provided. In this regard, the method comprises providing at least a first green sheet, forming a metal layer on a first surface of the first green sheet, and forming a blank by applying a green sheet stack comprising second green sheets on the first surface. Further, the method comprises debinding the blank and then sintering the blank, wherein a dielectric layer having a thickness D is formed from the one or more first green sheets by the sintering. The thickness D in this case is ≤150 μm.

In principle, therefore, the dielectric layer can be formed from a single first green sheet. Alternatively, however, several first green sheets can be provided together, from which the dielectric layer is formed by the above-mentioned process. Preferably, however, the number of green sheets is small, i.e., preferably a single green sheet to four green sheets. The number and thickness of the green sheets must be selected so that the dielectric layer reaches a thickness D≤150 μm.

Preferably, the above-described aspect produces the above-described support element from the green sheet stack by debinding and in particular by sintering.

During sintering, the electrode layer of the ceramic electrode is preferably formed from the metal layer.

Preferably, the materials described above in connection with the ceramic electrode are used in particular for the dielectric layer. In such a case, sintering temperatures can be applied, for example, in a range from 1000 to 1500° C., preferably in a range from 1400 to 1450° C.

Depending on the method of applying the metal layer, the electrode layer as described above can be produced from this metal layer by debinding and sintering. This is particularly the case if the metal layer is formed by printing with a metal paste which is converted into the electrode layer by sintering.

In order to withstand high temperatures, the metal layer and thus the electrode layer can, for example, be formed from a material comprising or consisting of palladium. In the case of an expensive material such as palladium, it is preferable that the metal layer or the electrode layer is formed very thinly.

When adjusting the dimensions of the components used in the process, sintering shrinkage may have to be taken into account in order to obtain preferred dimensions of a ceramic electrode according to the invention.

In this way, the appropriate process can be used to produce a component with the advantages described above.

According to a preferred aspect of the method of manufacturing a ceramic electrode, the metal layer is formed on the first surface of the first green sheet such that a free area of the first surface remains free of the metal layer. In this case, the green sheet stack is and can be applied such that it is in direct mechanical contact with this free area.

Thus, the first green sheet or the material of the first green sheet, which is preferably a ceramic material, is in contact with the green sheet stack, for example the material of the second green sheets, which can preferably also be the same material as the material of the first green sheet. As a result, the green sheet stack can be efficiently sintered with the first green sheet, which means that a stable bond can be formed here by sintering.

According to another preferred aspect of the process, the green sheet stack comprises a cavity, or the green sheet stack is formed with, or comprises, a cavity in preparation for the process.

In this context, a cavity can be understood to mean that an opening in the stacking direction passes completely through the green sheet stack in the thickness direction.

In this context, it may be preferred that the cavity in the green sheet stack is filled with a metallic material. When applying the green sheet stack, i.e. when forming the blank, the green sheet stack is then applied in such a way that the cavity filled with a metallic material is brought into contact with the metal layer, i.e. the metallic material is brought into contact with the metal layer.

Sintering thus produces a strong bond between the metal layer and the metallic material.

The metallic material can be a via or, alternatively, a via can be formed from it during sintering.

According to another preferred aspect of the process, the green sheet stack may include a cavity. However, in this case the cavity is not filled with a metallic material prior to sintering. Thus, the cavity forms an opening towards which the metal layer or the electrode layer formed in this way is exposed after sintering, and this is contacted after sintering by forming a contact layer.

In this case, the contact layer can correspond to the contact component or be the contact component.

The contact layer can be formed, for example, by sputtering, by means of an electroplating process or by screen printing a metal paste and subsequent baking.

These alternative processes for forming a contact component or the contact component itself thus created each have different advantages.

A solid, i.e. all-metal via as described above has the advantage that it is easier to manufacture, i.e. it can be introduced during the process steps required to process the ceramic components anyway.

The advantage of forming a contact layer as a contact component is that no massive heavy material has to be used. In addition, a material can be used that is not exposed to the extreme conditions of the sintering process or does not have to withstand them. This results in a higher degree of material freedom. In addition, costs can be saved by using less material and a lighter component can be formed.

If a cavity is left open during the sintering process, as in the latter case, this can affect the stability of the blank during the process.

To increase the stability of the green sheet stack or the blank, the cavity can preferably be filled with a polymer paste before the green sheet stack is applied. This polymer paste can be removed again during debinding and/or during sintering, preferably together with other organic components which are removed from the green sheets during these process steps.

Preferably, complete removal takes place during debinding, but residues may also leave the nascent ceramic electrode during sintering under certain circumstances.

The polymer paste may have, for example, polypropylene carbonate.

According to a further aspect of the present invention, a further method or a further process variant for producing a ceramic electrode, which may be, for example, a ceramic electrode described above, is described.

According to this process, a green sheet stack comprising second green sheets is preferably provided first. This green sheet stack is structured, whereby cavities and preliminary support elements are formed. Here, the structuring can be done such that a regular pattern of cavities and preliminary support elements is formed. For example, in a regular pattern, the formed cavities may be separated from each other by the preliminary support element. Further, the method comprises forming a blank by applying one or more first green sheets to the patterned green sheet stack, wherein a first surface of the first green sheet is in contact with the patterned green sheet stack. Further, in the method, the resulting blank is debonded and the blank is then subsequently sintered, wherein a dielectric layer having a thickness D is formed from the one or more first green sheets by the sintering, wherein the thickness D is less than or equal to 150 μm, and subsequently a metal layer may be formed. This is preferably formed on the first surface of the first green sheet, with a free area of the dielectric layer remaining free of the metal layer. In addition, a contact layer can be formed at the same time.

In this case, the same basic requirements apply to the selection of whether the dielectric layer is formed from one or more first green sheets as were mentioned for the process described above.

In addition, the sintering process preferably forms the support element of the ceramic electrode from the preliminary support element.

The present process may have the advantage that it can be used to simultaneously create a large number of cavities, which are separated from each other in a regular pattern by the support element, for example. Thus, good stability can be achieved.

Otherwise, the materials or the functions can correspond to those of the other process specified above.

Similar to what is described in connection with the other process, the cavities created after patterning can also be filled with a polymer paste, which is preferably removed during debinding and/or sintering.

The polymer paste used in this process can be the same as that used in the process described above and has similar advantages.

According to a preferred aspect of the method, patterning can be performed using a stamping process or a laser process. Stamping processes and laser processes are particularly preferred long-range processes that can produce extended regular patterns that can create a plurality of cavities, thereby producing a plurality of ceramic electrodes.

Another advantage of the last described process is that the metal layer, i.e. the layer which becomes the electrode layer or which can be the electrode layers, can be carried out simultaneously or in the same process step of forming a contact layer.

In particular, a significantly wider cavity can be left open in the above process than is possible in the previously described process. The resulting area is large enough to subsequently produce the electrode layer on the bottom of the cavity, i.e., on an area of the first surface of the first green sheet or the dielectric layer.

Preferably, the metal layer, but also the contact layer, can be applied here by sputtering, by an electroplating process or by screen printing.

According to a preferred aspect, which relates to all processes or embodiments of processes described herein, the free area may have a width which is greater than or equal to the thickness of the dielectric layer. Approximately this provides the advantages associated with the ceramic electrode.

Equivalently, the resulting and formed support element can thus also have a width that is at least equal to the thickness of the dielectric layer or has at least this thickness.

In the following, the invention will be explained in more detail by means of exemplary embodiments and the associated figures. Unless they are measurement results, the figures are schematic and may not be to scale for better understanding.

FIG. 1 shows a first embodiment of a ceramic electrode in schematic cross-section (FIG. 1A) and in schematic top view (FIG. 1B)

FIG. 2 shows a second embodiment of a ceramic electrode in schematic cross-section.

FIG. 6 shows in FIGS. 6a to f process steps for manufacturing a ceramic electrode according to the fourth embodiment in schematic cross-section.

Figure 7:
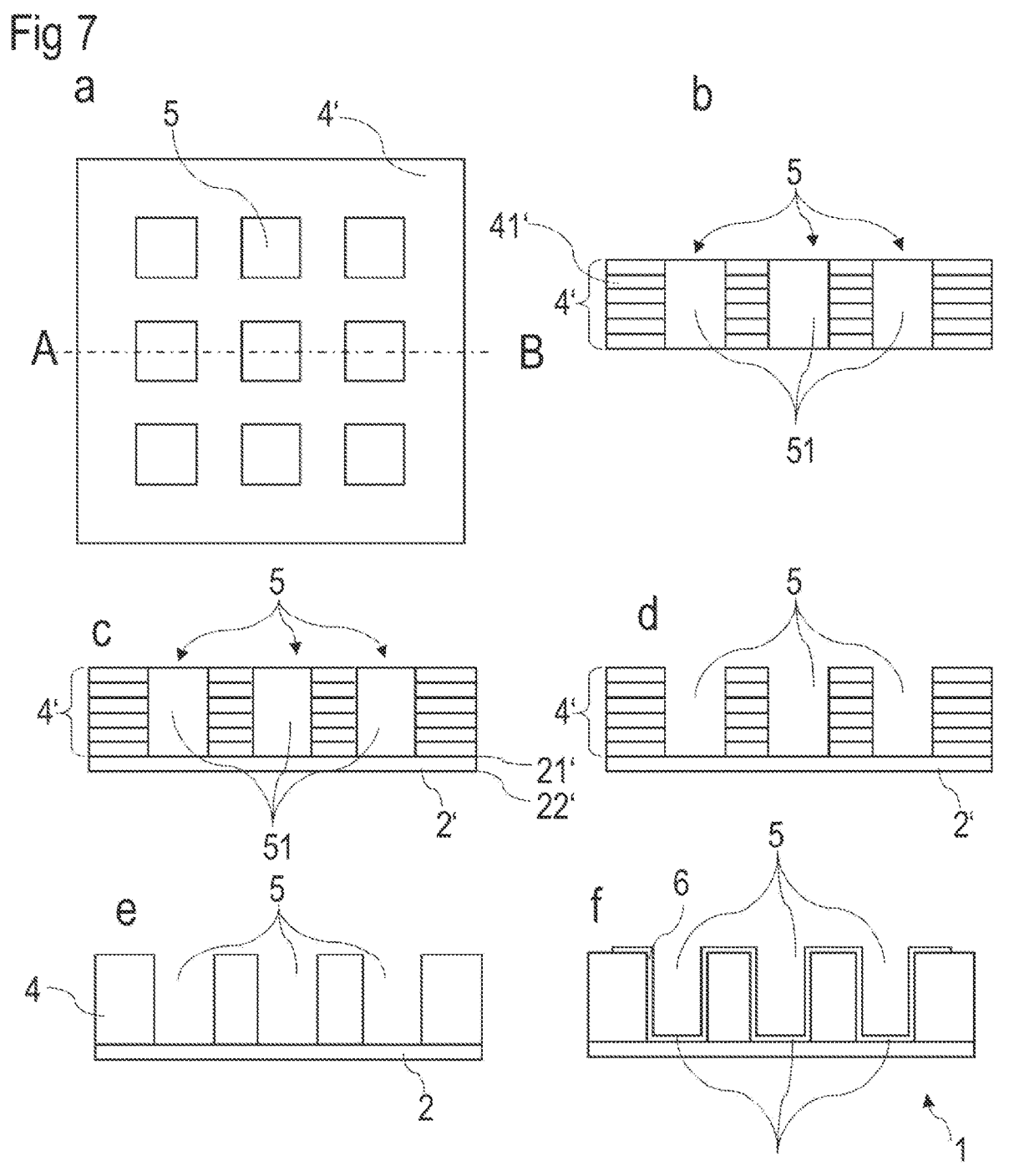

FIG. 7 shows in FIGS. 7a to f process steps for manufacturing a ceramic electrode according to a sixth embodiment in schematic cross-section.

FIG. 8 shows the temperature dependence of the capacitance (FIG. 8a) and the dissipation factor FIG. 8b for two ceramic electrodes according to the second embodiment.

FIG. 9 shows the temperature dependence of the capacitance (FIG. 9a) and the dissipation factor FIG. 9b for two ceramic electrodes according to the sixth embodiment.

Figure 3:
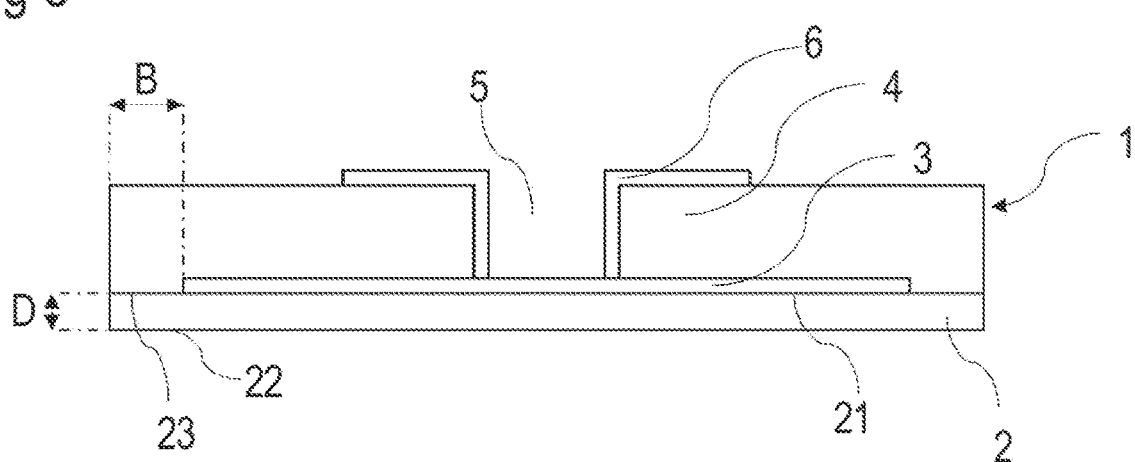
FIG. 3 shows a third embodiment of a ceramic electrode in schematic cross-section.

FIG. 1 shows a first embodiment of a ceramic electrode 1 according to the present invention. Here, FIG. 1A shows a schematic cross-section of the ceramic electrode 1 and FIG. 1B shows a schematic top view of the ceramic electrode 1.

The ceramic electrode 1 has a dielectric layer 2. The dielectric layer 2 preferably consists of a ceramic material with a high dielectric constant preferably greater than 15000.

For example, the ceramic material of the dielectric layer 2 may be a material of $(1-y)[Pb_a(Mg_bNb_c)O_{3-e}]+y$ $[Pb_aTi_dO_3]$ or a material of $Ba_m(Ti_nZr_p)O_3$ with a doping comprising manganese and a rare earth element.

The dielectric layer 2 can have any shape. Preferably, the dielectric layer 2 can be rectangular, square or, as in the case shown, circular, with a planar shape. That is, it has a lateral extent that is far greater than the thickness.

For example, the dielectric layer may have an area of 15 to 100 $mm^2$. Preferably, the area can be between 20 and 50 $mm^2$, for example 36 $mm^2$.

The dielectric layer is relatively thin compared to the conventional dielectric layer. The dielectric layer has the thickness D, which is less than 150 μm.

Preferably, the thickness D is between 20 and 100 μm, for example, the thickness D can be 40 μm. Alternatively, the thickness D can also be 80 μm.

Furthermore, the dielectric layer 2 has a first surface 21 and a second surface 22. The second surface 22 is the surface which faces towards the patient in an application, for example, for tumor treatment.

In the first embodiment of the present invention, an electrode layer 3 is arranged on the first surface 21 of the dielectric layer 2. Preferably, the electrode layer 3 has the same basic shape as the dielectric layer 2 and may be arranged centered with respect thereto. In the present case, therefore, the electrode layer 3 is disc-shaped or circular and arranged centered on the dielectric layer 2.

However, the area in the direction of extension of the dielectric layer 2, which is the direction of extension of the electrode layer 3, is smaller than the area of the dielectric layer 2. As a result, a free area 23 of the first surface 21 of the dielectric layer 2 remains free of the electrode or is not covered by the electrode 3 in this free area.

In the present embodiment example, the free area is a lateral edge region of the dielectric layer. This means that in this case the free area is in direct contact with the edge of the dielectric layer 2.

In the present embodiment, the electrode layer 3 and the dielectric layer 2 have the same shape and are centered on each other, so that the lateral edge region or the free area has an annular shape that extends along the entire outer edge of the dielectric layer 2.

The inventors of the present invention have found that the edge region preferably has a width B which corresponds to at least one thickness D of the dielectric layer, or, respectively, B is greater than or equal to D.

The width is measured in a direction parallel to the direction of extension of the dielectric layer 2. In a point-symmetric shape such as a circle, the direction of the width B is preferably measured in the direction of the center of the circle. In a rectangle or a square, the width B is preferably measured in a direction perpendicular to the outer edge of the rectangle or square.

Preferably, B is larger than 50 μm even more preferably wider than 100 μm. Preferably, B can be smaller than 1.5 mm, for example smaller than 1 mm.

The wider B is, the more stabilizing reinforcing elements or a support element in contact with it can act. However, B should not be too large, otherwise the active area, which is defined by the electrode area, is excessively reduced, which can have a negative effect on the overall capacity of the component.

Furthermore, a support element 4 is arranged on the first surface 21 of the dielectric layer 2.

The support element 4 preferably has a ceramic material similar or identical to that of the dielectric layer 2. However, it can also be made of any other material, for example a ceramic material, which is well suited to be firmly baked with the ceramic material of the dielectric layer 2 by sintering.

The support element should be in direct physical contact with at least parts of the free area 23 in order to be efficiently bonded to the ceramic of the dielectric layer 2. Preferably, as shown in the present embodiment, the support element 4 is designed to completely cover the free area 23.

Furthermore, the support element 4 is also formed here on parts of the electrode layer 3. Due to the overlap with the electrode layer 3, a larger area is covered by the support element 4 and can thus be efficiently supported by it.

Furthermore, the support element 4 has a cavity 5. The cavity 5 extends through the entire support element in a direction perpendicular to the direction in which the dielectric layer 2 extends, i.e., in the thickness direction. The electrode layer 3 is exposed at the bottom of this cavity 5. It is therefore possible to make electrical contact with the electrode layer 3 from the outside via cavity 5 or to establish contact with it in an application.

Thus, the support element 4 preferably has the same or a similar shape as the dielectric layer 2.

A thickness of the support element 4 is preferably at least as great as the thickness D of the dielectric layer 2. Preferably, however, the thickness of the support element is significantly greater. For example, the thickness of the support element may be between 100 μm and 1000 μm, preferably the thickness of the support element may be 200 μm to 700 μm. For example, the thickness of the support element can also be 400 μm to 600 μm, for example about 500±30 μm.

FIG. 2 shows a second embodiment of a ceramic electrode according to the invention in schematic cross-section. The second embodiment of the ceramic electrode corresponds largely to that shown in FIG. 1A. However, in contrast to the ceramic electrode shown in FIG. 1A, the second embodiment of a ceramic electrode has a contact component 6. In the present embodiment, this contact component 6 is formed as a via in the support element 4. The via fills the cavity 5 in the support element 4.

The via is preferably made of a conductive metal preferably palladium, as this is particularly suitable for manufacturing processes described below. For example, the via can be made from a metal paste containing palladium.

The via contacts the electrode layers 3. In addition, because it is at least flush with the surface of the support element, it is suitable for the ceramic electrode to be inserted, for example soldered, into an application via the upper side of the via.

In such a soldering step, the ceramic of the support element 4 can be protected, for example, by a solder resistor.

FIG. 3 shows a third embodiment of a ceramic electrode according to the present invention, which may also predominantly correspond to the embodiment shown in FIG. 1.

Here, too, a contact component 6 is formed in addition to the components of the first embodiment. This is formed as a contact layer which covers the walls of the cavity 5 and parts of the surface of the support element 4. Here, too, this enables electrical contacting of the electrode layer 3.

As described below, the contact layer or the contact component 6 can be produced by various methods. The contact layer shown herein preferably comprises a conductive material or comprises one or more conductive materials. The conductive materials are preferably selected from chromium, nickel, tin and palladium. For example, a thin layer of chromium and/or nickel may be in direct contact with the support element 4 on which a nickel or nickel/tin layer is then deposited.

The horizontal parts of the contact component 6 shown can again serve as a soldering surface.

Figure 4:
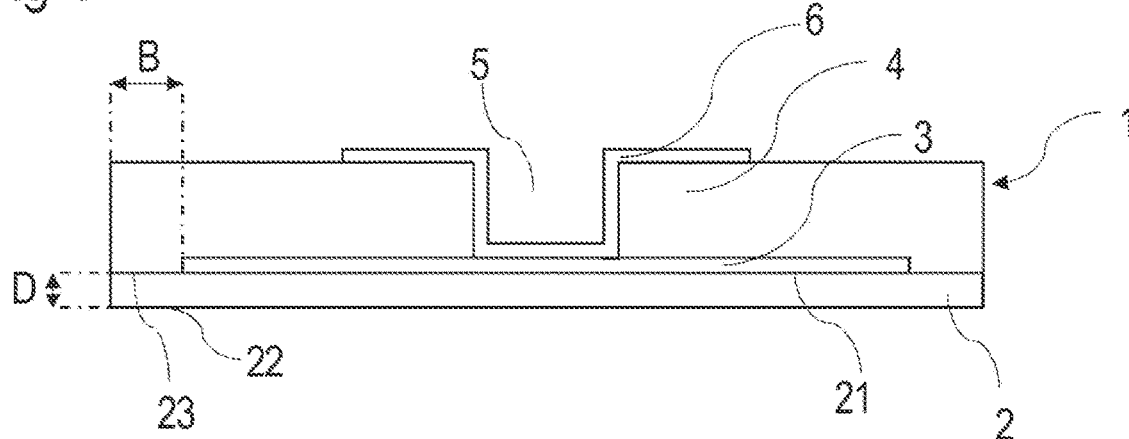
FIG. 4 shows a fourth embodiment of a ceramic electrode in schematic cross-section.

FIG. 4 shows a variant of the third embodiment as a fourth embodiment.

In the fourth embodiment, the contact component 6 is formed as a continuous layer and thus also covers the otherwise exposed part of the electrode layer 3.

This can have the advantage that a process for producing the contact layer can be carried out more easily. In addition, the contact component 6 can thus protect the material of the electrode layer from the outside. In addition, a more stable electrical contact can be achieved due to the more planar connection.

Figure 5:
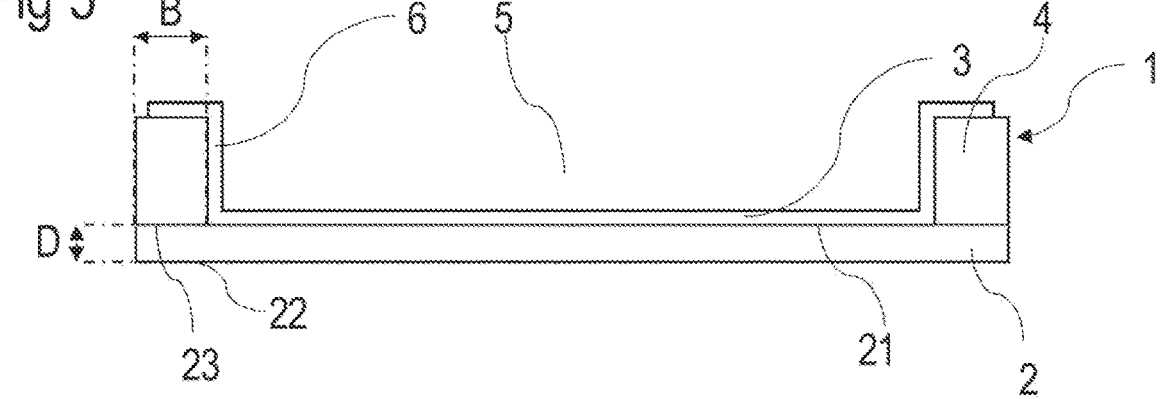
FIG. 5 shows a fifth embodiment of a ceramic electrode in schematic cross-section.

In FIG. 5, a fifth embodiment of a ceramic electrode according to the present invention is shown in schematic cross-section.

In principle, the ceramic electrode shown in FIG. 5 can largely correspond to the previously mentioned electrodes.

However, the ceramic electrode shown in FIG. 5 differs in the following properties, among others.

As can be seen in FIG. 5, the support element 4 is formed exclusively in the free area 23 or in the lateral edge region of the first surface 21 of the dielectric layer 2. The cavity 5 left open by the support element 4 is significantly wider than in the previous examples and corresponds in this case to the width or diameter of the electrode layer 3.

The electrode layer 3 is formed as a common layer together with the contact component 6. The electrode layer 3 preferably covers the entire bottom of the opening 5 or the entire area of the first surface 21 of the dielectric layer 2, which is not covered by the support element 4.

The contact component 6 is represented here by the areas arranged on the side walls of the opening or of the support element 4 and by the areas arranged on the support element 4. The contact component 6 is formed here as a common layer with the electrode layer 3.

This shape with a large cavity can have several advantages. Firstly, the support element 4 is less massive or voluminous and is largely just a frame which extends along the outer edge of the dielectric layer 2.

Furthermore, there may be advantages for the process as also shown below, since the electrode layer 3 and the contact component 6 can be produced in a common step, i.e. as a common single layer or multilayer.

Figure 6:
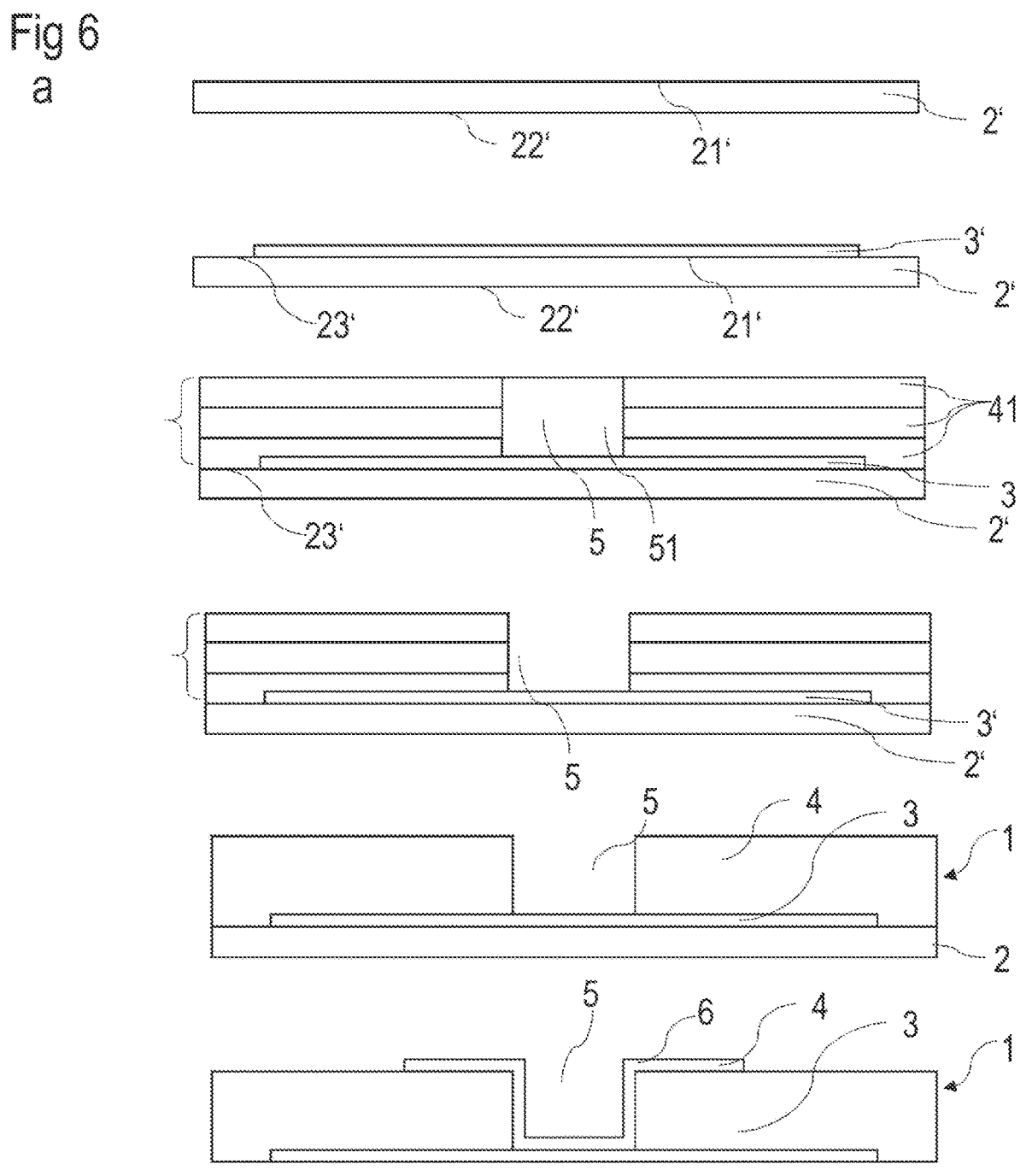

FIG. 6 shows in FIGS. 6A to 6F steps of a manufacturing process of a ceramic electrode as shown, among others, in FIG. 4. It can also be used in adapted form for manufacturing the embodiments of FIGS. 1 to 3.

FIG. 6A shows a first green sheet 2' which is provided, for example, on a support sheet (not shown). The first green sheet 2' has a first surface 21' and a second surface 22'. Alternatively, instead of the first green sheet 2', two first green sheets or a plurality of first green sheets can be used. The only important factor here is that, adjusted for sinter shrinkage, the thickness of the plurality of first green sheets or the thickness of the one first green sheet is less than or equal to 150 μm.

A variant in which a single or two first green sheets are used is particularly preferred.

A metal layer 3' is provided on the first surface 21' of the first green sheet 2', as shown in FIG. 6b. Preferably, the metal layer 3' is produced by printing with a metal paste, which preferably contains palladium or another temperature-resistant metal.

As shown in FIG. 6c, in a next step a green sheet stack 4' comprising a plurality of second green sheets 41' or consisting of a plurality of second green sheets 41' is provided. Preferably, the green sheet stack 4' has a cavity 5 which is preferably filled with a polymer paste 51, for example comprising polypropylene carbonate.

The second green sheet 41' can, for example, largely correspond to the first green sheet 2' except for the recesses forming the cavity 5.

Alternatively, the second green sheets 41' are made of a ceramic material that is particularly suitable for being baked with the ceramic material of the first green sheet 2'.

In particular, there is contact between the green sheet stack 4' and the first surface 21' of the first green sheet 2' in a free area 23' of the first surface 21' of the first green sheet 2'.

In a later step, this contact enables the first green sheet to be firmly and thus stably bonded to the green sheet stack.

In a next step (FIG. 6d), the green sheet stack is debinded, whereby organic components are removed from the green sheet stacks or the green sheets. In this process, the polymer paste is also largely or completely removed.

Subsequently, as shown in FIG. 6e, the debinded blank is sintered. This forms the dielectric layer 2 from the first green sheet 2' or from several first green sheets 2'. The electrode layer 3 is formed from the metal layer 3'. The green sheet stack 4' is sintered to form the support element 4. Thus, a ceramic electrode 1 can be obtained as shown, for example, in FIG. 1.

In a further step, as shown in FIG. 6f, a contact component 6 can be applied to the ceramic electrode produced in FIG. 6e.

The contact layer or contact component 6 can be produced by screen printing and subsequent baking of a metal-containing paste. A baking temperature here can be 680 to 760° C., for example. Alternatively, a sputtering process can be used. Furthermore, an electroplating process can be used to produce the contact layer or the contact component 6, whereby a seed layer can first be applied, for example by sputtering, and then the contact layer is grown by an electrochemical or electroplating process. Alternatively, electroless plating can also be used.

FIG. 7 and FIGS. 7a to f show a further process which can be used in modified form, inter alia, for the production of a ceramic electrode according to the invention as shown in FIG. 5. Otherwise, the sixth embodiment of a ceramic electrode described below (FIG. 7f) can be produced by the process shown in FIG. 7.

In a first step, a green sheet stack 4' is provided for the production of a ceramic electrode (green sheet stack not explicitly shown).

The green sheet stack 4' can be square, for example, and have a dimension of 4×4 mm 2 to 8×8 mm$^2$ for example 6.5×6.5 mm$^2$. The green sheet stack 4' comprises second green sheets 41' or consists of second green sheets 41'.

The process can also be used in multiples, i.e. to produce a large number of ceramic electrodes simultaneously. In this case, the individual green sheet stacks are separated, i.e. singled, in one of the following steps.

A next step is shown in FIGS. 7a and b.

The green sheet stack 4' is structured in a structuring process in such a way that cavities 5 are formed in the second green sheet stack 4', which extend vertically through the green sheet stack 4' in the thickness direction. The cavities 5 preferably form a regular pattern in the green sheet stack 4'.

FIG. 7a shows the structured green sheet stack 4' in plan view and FIG. 7b shows it in schematic cross-section along the line of intersection A-B in FIG. 7a.

To increase stability during the process, the cavities 5 may be filled with a polymer paste 51.

For structuring, a stamping process and a laser process are preferably used. These structuring methods are well suited for the production of regular patterns.

A punching process or a laser process can be used to simultaneously structure a large number of green sheet stacks 4'. This is particularly suitable for producing a large number of uniform ceramic electrodes of the same quality.

In a further process step, shown in FIG. 7c, one or more first green sheets 2' are attached to the green sheet stack 4'. In the present example, only a single green sheet 2' is shown. This forms a blank.

The structured green sheet stack 4' has the above-mentioned cavities 5. The remaining ceramic material from the green sheet stack can be considered here as a preliminary support element, since support element 4 is formed from these remaining structures of green sheet stack 4' by sintering, as described below.

As shown in FIG. 7d in schematic cross-section, in the next step the previously produced blank can be debinded, whereby, among other things, the polymer material 51 is removed. Thus, the cavities are preferably open after debinding so that the first surface 21' of the first green sheets 2' is exposed in them.

In a sintering step (FIG. 7e), a dielectric layer 2 is formed from the first green sheet 2' or from several first green sheets 2'. The green sheet stack 4' or the preliminary support element has been sintered to form the support element 4.

The support element 4 has a structure similar to that shown in FIG. 7a for the structured green sheet stack. A grid has thus been created by the support element 4, whereby the support element 4 forms walls which separate the cavities 5 from one another.

The resulting cavities may have a cross-sectional area from 0.06 mm 2 to 5 mm$^2$ preferably from 0.25 mm 2 to 2.25 mm 2 or more preferably from 0.55 mm 2 to 1.5 mm$^2$ for example 1 mm$^2$.

The width dimensions of the support element or the parts separating the cavities 5 from each other is in any case greater than the thickness D of the dielectric layer, for example it can be 0.2 mm to 1.5 mm preferably 0.5 mm to 1.25 mm, for example 0.75 mm.

A thickness of the support element between the outermost cavities 5 and the edge of the dielectric layer can also lie in the above-mentioned ranges. However, the support element can preferably be somewhat thicker here, for example 25 to 50% thicker. The support element can be 1 mm thick towards the edge, for example.

The framing that results with the structuring shown above is not mandatory, but preferred. This can increase stability because the framing means that the dielectric layer is not exposed at the edges or corners.

The parts of the support element 4, which are located between the cavities, further increase the mechanical stability, since a large-area free-floating dielectric layer 2 is prevented.

In a further final step F, a metal layer 3', i.e. an electrode layer 3, can be formed simultaneously with a contact component 6, which in this case is a contact layer. This can be formed in a similar way to that described for FIG. 5. In particular, sputtering, burning in of a paste or/and an electroplating process can be used here.

Thus, a ceramic electrode 1 can be formed with a plurality of cavities.

In the present embodiment, the number of cavities is 9. However, analogously, any pattern can be made with a single cavity similar to the design shown in FIG. 5 to a plurality of cavities, such as 2, 3, 8, 9, 12 or 16.

FIG. 8a shows a graph showing the dependence of the capacitance of two ceramic electrodes according to the invention, as shown in FIG. 4, on temperature.

The dielectric layer thicknesses used here were about 80 μm for both ceramic electrodes. The active electrode area or the area of the electrode layer was about 20 mm$^2$.

The graph shown in FIG. 8a shows, regardless of slight variations due to the laboratory procedure, that in the relevant temperature range, i.e. between 30° C. and 40° C., a capacitance of more than 20 nF or even almost up to 30 nF can be achieved.

FIG. 8b also shows the dependence of the loss factor tan δ on temperature for these ceramic electrodes. For the relevant temperature range of 30° C. to 40° C., a dissipation factor of well below 0.04 is achieved in both cases.

This shows that the loss factors are not affected by the current design, making it possible to produce a high quality electrode.

FIG. 9a shows the temperature dependence of the capacitance of two ceramic electrodes according to the invention, which were manufactured according to the embodiment shown in FIG. 7f.

In particular, there was a dielectric thickness of 0.072 mm, i.e. 72 μm, which was produced from two first green sheets with a thickness of 40 μm each. The total area of the dielectric layer covered with an electrode layer 3 was about 9×13 mm$^2$. The rest of the area was covered by the support element. This corresponds to an area utilization, i.e. coverage with an electrode layer, of 36%.

The graph shown in FIG. 9a shows that a capacitance of almost 30 nF can be achieved for both samples in the relevant temperature range between 30 and 40° C. The capacitance of the two samples can be measured in the same way.

This shows that a highly efficient ceramic electrode can be formed with an electrode configuration with a large number of cavities as shown in FIG. 7f. Furthermore, it can be shown that a high-capacity electrode can be produced with an electrode area of approximately 35 mm$^2$, which is thus significantly smaller than the electrodes used to date.

FIG. 9b shows the temperature dependence of the loss factor tan δ for the embodiments of FIG. 9b, which in this case is also about 0.02 or even lower in the relevant temperature range between 30 and 40° C. The temperature dependence of the loss factor tan δ is also shown in FIG. 9b.

LIST OF REFERENCE SIGNS

1 Ceramic electrode
2 Dielectric layer
2' First green sheet
3 Electrode layer
3' Metal layer
4 Support element
4' Green sheet stack
5 Cavity
6 Contact component
21 first surface of the dielectric layer
21' first surface of the first green sheet
22 second surface of the dielectric layer
22' second surface of the first green sheet
23 Free area of the dielectric layer
23' Free area of the first green sheet
41' second green sheet
51 Polymer paste
D Thickness of the dielectric layer
B Width of the free area

The invention claimed is:

1. A ceramic electrode comprising
a support element as a mechanically stabilizing component,
a dielectric layer having a thickness, D, less than or equal to 150 μm, and
an electrode layer
arranged on and partially covering a first surface of said dielectric layer, a free area of the first surface of the dielectric layer being free of the electrode layer and the support element being in contact with this free area, the free area having a width greater than or equal to the thickness of the dielectric layer, wherein the width corresponds to an extension in the lateral direction,
wherein the dielectric layer comprises a ceramic material having a dielectric constant greater than or equal to 15000.

2. The ceramic electrode according to claim 1, wherein the free area is a lateral edge region of the dielectric layer.

3. The ceramic electrode according to claim 1, wherein a width of the support element is greater than or equal to the thickness of the dielectric layer.

4. The ceramic electrode according to claim 1, which has a contact component that electrically contacts the electrode layer.

5. The ceramic electrode according to claim 1, wherein 20 μm≤D≤100 μm.

6. The ceramic electrode according to claim 1, wherein the ceramic material is selected from $(1-y)[Pb_a(Mg_bNb_c)O_{3-e}]+y[Pb_aTi_dO_3]$ and $Ba_m(Ti_nZr_p)O_3$ with a doping comprising manganese and a rare earth element.

7. The ceramic electrode according to claim 1, having a cross-sectional area between 15 and 100 mm$^2$ and a maximum thickness of 300 to 700 μm.

8. The ceramic electrode according to claim 1, which is configured and suitable for attachment to the human body or parts of the human body.

9. The ceramic electrode according to claim 1, wherein the ceramic electrode comprises one or more cavities in the support element.

10. The ceramic electrode according to claim 9, wherein the electrode layer is exposed within the cavity or is in direct contact with a filling of the cavity.

11. The ceramic electrode according to claim 9, wherein a regular pattern of cavities is formed, whereby a grid is formed by the support element, which frames the individual cavities.

12. An assembly comprising a ceramic electrode arranged on a flexible board according to claim 1.

13. An array comprising a plurality of ceramic electrodes according to claim 1.

14. A method of manufacturing a ceramic electrode, comprising the steps of:
   A Providing at least one first green sheet,
   B Forming a metal layer on a first surface of the at least one first green sheet,
   C Forming a blank by applying a green sheet stack comprising second green sheets to the first surface,
   D Debinding of the blank, and
   E Sintering the blank, wherein the sintering forms a dielectric layer having a thickness from the first green sheet or sheets, wherein the thickness is less than or equal to 150 μm, wherein the metal layer partially covers said the surface of the dielectric layer, wherein a free area of the first surface of the dielectric layer is free of the metal layer and the green film stack is in contact with the free area, said free area having a width greater than or equal to the thickness of said dielectric layer, said width corresponding to an extension in lateral direction, wherein the dielectric layer comprises a ceramic material having a dielectric constant greater than or equal to 15000.

15. A method of manufacturing a ceramic electrode according to claim 14, wherein the metal layer is formed on the first surface such that a free area of the first surface remains free of the metal layer, and the green sheet stack is applied so that it is in contact with the free area.

16. A method of manufacturing a ceramic electrode according to claim 14, wherein the green sheet stack has a cavity which is filled with a metallic material before the green sheet stack is applied, and the metallic material is in contact with the metal layer.

17. A method of manufacturing a ceramic electrode according to claim 14, wherein the green sheet stack comprises a cavity in which, after sintering, a contact layer is formed, which contacts the metal layer.

18. A method of manufacturing a ceramic electrode according to claim 17, wherein the cavity is filled with a polymer paste prior to the application of the green sheet stack, which is removed by debinding and/or sintering.

19. A method of manufacturing a ceramic electrode, comprising the steps of:
   A Providing a green sheet stack comprising second green sheets,
   B Structuring of the green sheet stack with formation of cavities and temporary support elements,
   C Forming a blank by applying at least a first green sheet to the structured green sheet stack, wherein a first surface of the first green sheet is in contact with the structured green sheet stack,
   D Debinding of the blank,
   E Sintering of the blank, said sintering forming a dielectric layer having a thickness from the first green sheet or sheets, the thickness (D) being less than or equal to 150 μm, and
   F Forming a metal layer on the first surface of the first green sheet, wherein a free area of the dielectric layer remains free of the metal layer, and forming a contact layer, wherein
   the green film stack is in contact with the free area, wherein the free area has a width greater than or equal to the thickness of said dielectric layer, said width corresponding to an extension in the lateral direction.

20. A method of manufacturing a ceramic electrode according to claim 19, wherein the cavities are filled with a polymer paste after the structuring, which is removed by debinding and/or sintering.

21. A method of manufacturing a ceramic electrode according to claim 19, wherein the structuring is carried out by means of a stamping process or a laser process.

22. A method of manufacturing a ceramic electrode according to claim 19, wherein the free area has a width which is greater than or equal to the thickness of the dielectric layer.

23. A method of manufacturing a ceramic electrode according to claim 19, wherein the formation of the metal layer is carried out by sputtering, an electroplating process or screen printing.

24. An assembly comprising a ceramic electrode arranged on a flexible board, the ceramic electrode including:
   a support element as a mechanically stabilizing component,
   a dielectric layer having a thickness less than or equal to 150 μm, and
   an electrode layer
   arranged on and partially covering a first surface of said dielectric layer, a free area of the first surface of the dielectric layer being free of the electrode layer and the support element being in contact with this free area, the free area having a width greater than or equal to the thickness of the dielectric layer, wherein the width corresponds to an extension in the lateral direction.

25. A method of manufacturing a ceramic electrode arranged on a flexible board, the method comprising the steps of:
   A Providing at least one first green sheet,
   B Forming a metal layer on a first surface of the at least one first green sheet,
   C Forming a blank by applying a green sheet stack comprising second green sheets to the first surface,
   D Debinding of the blank, and
   E Sintering the blank, wherein the sintering forms a dielectric layer having a thickness from the first green sheet or sheets, wherein the thickness is less than or equal to 150 μm, wherein the metal layer partially covers said the surface of the dielectric layer, wherein a free area of the first surface of the dielectric layer is free of the metal layer and the green film stack is in contact with the free area, said free area having a width greater than or equal to the thickness of said dielectric layer, said width corresponding to an extension in lateral direction.

26. A method of manufacturing a ceramic electrode, the method comprising the steps of:
   A Providing at least one first green sheet, B Forming a metal layer on a first surface of the at least one first green sheet, C Forming a blank by applying a green sheet stack comprising second green sheets to the first surface, D Debinding of the blank, and E Sintering the blank, wherein the sintering forms a dielectric layer having a thickness from the first green sheet or sheets, wherein the thickness is less than or equal to 150 µm, wherein the metal layer partially covers said the surface of the dielectric layer, wherein a free area of the first surface of the dielectric layer is free of the metal layer and the green film stack is in contact with the free area, said free area having a width greater than or equal to the thickness of said dielectric layer, said width corresponding to an extension in lateral direction, wherein the green sheet stack comprises a cavity in which, after sintering, a contact layer is formed, which contacts the metal layer, and wherein the cavity is filled with a polymer paste prior to the application of the green sheet stack, which is removed by debinding and/or sintering.

* * * * *